United States Patent

Sherman et al.

Patent Number: 6,099,737
Date of Patent: Aug. 8, 2000

[54] PROCESS FOR REMOVING TOXINS FROM BLOOD USING ZIRCONIUM METALLATE OR TITANIUM METALLATE COMPOSITIONS

[75] Inventors: John D. Sherman, Inverness; David S. Bem, Arlington Heights; Gregory J. Lewis, Mt. Prospect, all of Ill.

[73] Assignee: UOP LLC, Des Plaines, Ill.

[21] Appl. No.: 09/281,118

[22] Filed: Mar. 29, 1999

[51] Int. Cl.$^7$ ..................... B01D 15/04
[52] U.S. Cl. ............ 210/691; 210/903; 210/905; 210/908; 210/909
[58] Field of Search ................ 210/691, 903, 210/905, 908, 909, 681

[56] References Cited

U.S. PATENT DOCUMENTS

| | | | |
|---|---|---|---|
| 3,888,250 | 6/1975 | Hill | 210/694 |
| 4,118,314 | 10/1978 | Yoshida | 210/673 |
| 4,261,828 | 4/1981 | Brunner et al. | 210/287 |
| 4,581,141 | 4/1986 | Ash | 210/502 |
| 5,536,412 | 7/1996 | Ash | 210/645 |

*Primary Examiner*—Ivars Cintins
*Attorney, Agent, or Firm*—John G. Tolomei; Frank S. Molinaro

[57] ABSTRACT

A process for removing toxins from blood is disclosed. The process involves contacting the blood with a microporous ion exchanger to remove toxins in the blood. Alternatively, the blood can be contacted with a dialysis solution which is then contacted with the ion exchanger. The microporous ion exchangers are represented by the following empirical formulae:

$$A_pM_xZr_{1-x}Si_nGe_yO_m \qquad (I)$$

and $$A_pM_xTi_{1-x}Si_nGe_yO_m \qquad (II)$$

8 Claims, No Drawings

PROCESS FOR REMOVING TOXINS FROM BLOOD USING ZIRCONIUM METALLATE OR TITANIUM METALLATE COMPOSITIONS

FIELD OF THE INVENTION

This invention relates to an extracorporeal process for removing toxins from blood. The blood is either contacted directly with a microporous ion exchange composition which is capable of selectively removing the toxins from the blood or the blood is first contacted with a dialysis solution which is then contacted with the microporous ion exchange composition.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino-acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove.

The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940's.

The art contains a number of disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium exchanged zeolite. Finally, U.S. Pat. No. 5,536,412 discloses hemofiltration and plasmafiltration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood.

Applicants have developed a process which uses microporous ion exchangers which are essentially insoluble in blood or dialysis solutions. These microporous ion exchangers have an empirical formula on an anhydrous basis of:

$$A_pM_xZr_{1-x}Si_nGe_yO_m \quad (I)$$

or $$A_pM_xTi_{1-x}Si_nGe_yO_m \quad (II)$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$. The germanium can substitute for the silicon, zirconium/titanium or combinations thereof.

SUMMARY OF THE INVENTION

As stated, this invention relates to a process for removing toxins from blood. The process comprises contacting a fluid containing the toxins with a microporous ion exchanger at ion exchange conditions thereby removing the toxins from the fluid, the microporous ion exchanger selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

and $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$.

This and other objects and embodiments will become more clear after a detailed description of the invention.

DETAILED DESCRIPTION OF THE INVENTION

As stated, applicants have developed a new process for removing various toxins from blood. One essential element of the instant process is a microporous ion exchanger which has a large capacity and strong affinity, i.e., selectivity for at least ammonia. These microporous compositions are identified as zirconium metallate and titanium metallate compositions. They are further identified by their empirical formulas (on an anhydrous basis) which respectively are:

$$A_p M_x Zr_{1-x} Si_n Ge_y O_m \qquad (I)$$

or $$A_p M_x Ti_{1-x} Si_n Ge_y O_m \qquad (II)$$

In the case of formula I, the composition has a microporous framework structure composed of $ZrO_3$ octahedral units and at least one of $SiO_2$ tetrahedral units and $GeO_2$ tetrahedral units. In the case of formula II, the microporous framework structure is composed of $TiO_3$ octahedral units and at least one of $SiO_2$ tetrahedral units and $GeO_2$ tetrahedral units.

In both formulas I and II, A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from zero to less than 1, "n" has a value from about 0 to about 12, "y" has a value from 0 to about 12, "m" has a value from about 3 to about 36 and the sum of n+y has a value from about 1 to about 12. That is $1 \leq n+y \leq 12$. In equation (II) M is, of course, not titanium. The M metals which can be inserted into the framework in place of zirconium will be present as $MO_3$ octahedral units and thus it is a requirement that they are capable of being octahedrally coordinated. The germanium can be inserted into the framework in place of silicon and will be present as $MO_2$ tetrahedral units. Additionally, germanium can be inserted into the framework as a $MO_3$ octahedral unit replacing some of the zirconium in formula (I) or some of the titanium in formula (II). That is, germanium can replace some or all of the silicon, some of the zirconium in formula (I), some of the titanium in formula (II) or both silicon and zirconium or both silicon and titanium.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound which can be hydrolyzed to zirconium oxide or zirconium hydroxide can be used. Specific examples of these compounds include zirconium alkoxide, e.g., zirconium n-propoxide, zirconium hydroxide, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

The titanium metallates are prepared in an analagous manner to the zirconium metallates. Thus, the sources of silicon, germanium, M metal and alkali metal are as enumerated above. The titanium source is also as enumerated above, namely titanium alkoxides, titanium tetrachloride, titanium trichloride and titanium dioxide. A preferred titanium source is titanium alkoxides with specific examples being titanium isopropoxide, titanium ethoxide and titanium butoxide.

Generally, the hydrothermal process used to prepare the zirconium metallate or titanium metallate ion exchange compositions of this invention involves forming a reaction mixture which in terms of molar ratios of the oxides is expressed by the formulae:

$$aA_2O:bMO_{q/2}:1-bZrO_2:cSiO_2:dGeO_2:eH_2O \qquad (III)$$

and $$aA_2O:bMO_{q/2}:1-bTiO_2:cSiO_2:dGeO_2:eH_2O \qquad (IV)$$

where "a" has a value from about 0.25 to about 40, "b" has a value from about 0 to about 1, "q" is the valence of M, "c" has a value from about 0.5 to about 30, "d" has a value from about 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water and dried in air.

As stated the microporous compositions of this invention have a framework structure of octahedral $ZrO_3$ units, at least one of tetrahedral $SiO_2$ units and tetrahedral $GeO_2$ units and optionally octahedral $MO_3$ units. This framework results in a microporous structure having an intracrystalline pore system with uniform pore diameters, i.e., the pore sizes are crystallographically regular. The diameter of the pores can vary considerably from about 3Å and larger.

As synthesized, the microporous compositions of this invention will contain some of the alkali metal templating agent in the pores. These metals are described as exchangeable cations, meaning that they can be exchanged for other (secondary) cations. Generally, the A exchangeable cations can be exchanged for other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. The methods used to exchange one cation for another are well known in the art and involve contacting the microporous compositions with a solution containing the desired cation (at molar excess) at exchange conditions. Exchange conditions include a temperature of about 25° C. to about 100° C. and a time of about 20 minutes to about 2 hours. The particular cation (or mixture thereof) which is present in the final product will depend on the particular use and the specific composition being used.

It is also within the scope of the invention that these microporous ion exchange compositions can be used in powder form or can be formed into various shapes by means well known in the art. Examples of these various shapes include pills, extrudates, spheres, pellets and irregularly shaped particles.

As stated, these compositions have particular utility in adsorbing various toxins from blood. Generally, the contacting is carried out by means and apparati well known in the art. Thus, one technique is hemoperfusion which involves packing the above described microporous ion exchange composition into a column through which the blood is flowed. One such system is described in U.S. Pat. No. 4,261,828 which is incorporated by reference. As stated in the '828 patent, the microporous ion exchange composition is preferably formed into desired shapes such as spheres. Additionally, the microporous ion exchange composition particles can be coated with compounds, such as cellulose derivatives, which are compatible with the blood but non-permeable for corpuscular blood components. In one specific case, spheres of the desired ion exchange compositions described above can be packed into hollow fibers thereby providing a semipermeable membrane. It should also be pointed out that more than one type of molecular sieve can be mixed and used in the process in order to enhance the efficiency of the process.

Another way of carrying out the process is to prepare a suspension or slurry of the molecular sieve adsorbent by means known in the art such as described is U.S. Pat. No. 5,536,412 which is incorporated by reference. The apparatus described in the '412 patent can also be used to carry out the process. The process basically involves passing a fluid containing toxins through the interior of a hollow fiber and during said passing circulating a sorbent suspension against the exterior surfaces of the hollow fiber membrane. At the same time, intermittent pulses of positive pressure are applied to the sorbent solution so that the fluid alternately exits and re-enters the interior of the hollow fiber membrane thereby removing toxins from the fluid.

The instant microporous ion exchange compositions can also be used in a conventional dialysis process where the blood is first contacted with a dialysis solution (dialysate) to remove uremic substances from the blood. The dialysate is now regenerated and recirculated. Regeneration is carried out by contacting the urea containing dialysate with urease to convert the urea to ammonium ion and carbonate ion according to the equation:

$$2H_2O + H_4N_2CO \rightarrow 2NH_4^+ + CO_3^-$$

In order for this reaction to proceed to completion, ammonium ions and carbonate ions must be removed. In the instant process, the microporous ion exchangers have a large capacity and selectivity for removing ammonium ions from the dialysate fluid. The urease can of course be immobilized on the microporous ion exchange compositions of the present invention. Details regarding bonding of urease to microporous compositions can be found in U.S. Pat. No. 4,581,141 which is incorporated by reference.

As has also been stated, although the instant compositions are synthesized with a variety of exchangeable cations ("A"), it is preferred to exchange the cation with secondary cations which are more compatible with blood or do not adversely affect the blood. For this reason, preferred cations are sodium, calcium and magnesium. An especially preferred composition is one containing sodium and calcium. The relative amount of sodium and calcium can vary considerably and depends on the microporous composition and the concentration of these ions in the blood.

In order to more fully illustrate the invention, the following examples are set forth. It is to be understood that the examples are only by way of illustration and are not intended as an undue limitation on the broad scope of the invention as set forth in the appended claims.

EXAMPLE 1

A solution was prepared by mixing 2058 g of colloidal silica (DuPont Corp. identified as Ludox® AS-40), 2210 g of KOH in 7655 g H2O. After several minutes of vigorous stirring 1471 g of a zirconium acetate solution (22.1 wt. % $ZrO_2$) were added. This mixture was stirred for an additional 3 minutes and the resulting gel was transferred to a stainless steel reactor and hydrothermally reacted for 36 hours at 200° C. The reactor was cooled to room temperature and the mixture was vacuum filtered to isolate solids which were washed with deionized water and dried in air.

The solid reaction product was analyzed and found to contain 21.2 wt. % Si, 21.5 wt. % Zr, K 20.9 wt. % K, LOI 12.8 wt. %, which gave a formula of $K_{2.3}ZrSi_{3.2}O_{9.5}*3.7H_2O$. This product was identified as sample A.

EXAMPLE 2

A solution was prepared by mixing 121.5 g of colloidal silica (DuPont Corp. identified as Ludox® AS-40), 83.7 g of NaOH in 1051 g H2O. After several minutes of vigorous stirring 66.9 g zirconium acetate solution (22.1 wt. % $ZrO_2$) was added. This was stirred for an additional 3 minutes and the resulting gel was transferred to a stainless steel reactor and hydrothermally reacted 72 hours at 200° C. The reactor was cooled to room temperature and the mixture was vacuum filtered to isolate solids which were washed with deionized water and dried in air.

The solid reaction product was analyzed and found to contain 22.7 wt. % Si, 24.8 wt. % Zr, 12.8 wt. % Na, LOI 13.7 wt. %, which gives a formula $K_{2.0}ZrSi_{3.0}O_{9.0}*3.5H_2O$. This product was identified as sample B.

EXAMPLE 3

A solution (60.08 g) of colloidal silica (DuPont Corp. identified as Ludox® AS-40) was slowly added over a period of 15 minutes to a stirring solution of 64.52 g of KOH dissolved in 224 g deionized $H_2O$. This was followed by the addition of 45.61 g zirconium acetate (Aldrich 15–16 wt. % Zr, in dilute acetic acid). When this addition was complete, 4.75 g hydrous $Nb_2O_5$ (30 wt. % LOI) was added and stirred for an additional 5 minutes. The resulting gel was transferred to a stirred autoclave reactor and hydrothermally treated for 1 day at 200° C. After this time, the reactor was cooled to room temperature, the mixture was vacuum filtered, the solid washed with deionized water and dried in air.

The solid reaction product was analyzed and found to contain 20.3 wt. % Si, 15.6 wt. % Zr, 20.2 wt. % K, 6.60 wt. % Nb, LOI 9.32 wt. %, which give a formula of $K_{2.14}Zr_{0.71}Nb_{0.29}Si_3O_{9.2}*2.32$ $H_2O$. Scanning Electron Microscopy (SEM) of a portion of the sample, including EDAX of a crystal, indicated the presence of niobium, zirconium, and silicon framework elements. This product was identified as sample C.

EXAMPLE 4

$GeO_2$ (44.62 g) was slowly added to a stirring solution of 30.50 g of KOH dissolved in 140 g deionized $H_2O$. After the addition was complete, 45.82 g $ZrOCl_2*8H_2O$ dissolved in 140 g deionized H$_2$O was added drop-wise. The resulting gel was transferred to a stirred autoclave reactor and hydrothermally treated for 1 days at 200° C. After this time, the reactor was cooled to room temperature and the mixture was vacuum filtered, the solid was washed with deionized water and dried in air.

The solid reaction product was analyzed and found to contain 41.0 wt. % Ge, 18.4 wt. % Zr, 12.0 wt. % K, LOI 6.39 wt. %, which gave a formula of K$_{1.52}$ZrGe$_{2.80}$O$_{8.36}$•1.84H$_2$O. This product was identified as sample D.

EXAMPLE 5

Into a 2-liter beaker, 350.0 g of tetraethylorthosilicate (98%) and 160.83 g of titanium tetraisopropoxide (97%) were placed and stirred with a high speed mechanical mixer. Separately, 106.30 g KOH (87%) was dissolved in 768.5 g of deionized water. This solution was then added to the stirring alkoxides and agitated for an additional two hours. The reaction mixture was then transferred to a 2-liter stirred autoclave where it was digested at a temperature of 200° C. for 132 hr. while stirring at 100 rpm. The product was isolated by filtration, washed thoroughly with deionized water and dried at 100° C.

Elemental analysis of the product gave an empirical formula of K$_{1.95}$Si$_{2.94}$TiO$_{8.85}$. X-ray diffraction analysis showed that this product had the same topology as the mineral umbite. This product was identified as sample E.

EXAMPLE 6

Into a 2-liter beaker, there were mixed 380.0 g of tetraethylorthosilicate (98%) and 104.8 g of titanium tetraisopropoxide (97%). Separately, a sodium hydroxide solution was prepared by dissolving 58.90 g NaOH (97%) in 854.73 g deionized water. This solution was added to the alkoxide mixture as it was stirred vigorously with a mechanical stirrer. The reaction mixture was stirred for 2 hrs. before it was introduced into a 2-liter autoclave. The reaction mixture was reacted at 200° C. at autogenous pressure for 132 hrs. The product was isolated by filtration, washed with deionized water, and dried at 100° C.

Elemental analysis showed that this product had the empirical formula Na$_{2.05}$Si$_{3.72}$TiO$_{10.47}$. X-ray diffraction analysis showed that this product had the same topology as the mineral zorite. This product was identified as sample F.

EXAMPLE 7

Samples A to F and zeolite W (obtained from UOP LLC) were tested for removal of ammonium ions using the following procedure. If the compositions were not synthesized in the sodium form (zeolite W was obtained in the potassium form), the compositions were converted to the predominantly sodium form by contacting the compositions with a solution containing a molar excess (at least 10 fold) of sodium chloride thereby exchanging the sodium for the potassium. The exchange conditions were those typical in the art. A test solution was prepared by mixing 6 mL of a dialysate concentrate with 194 mL of deionized water and 0.7 g of ammonium chloride (NH$_4$Cl). The final composition of this dialysate test solution is shown in Table 1.

TABLE 1

Dialysate Test Solution Composition

| Element | mEq/L |
|---------|-------|
| Na      | 134   |
| Ca      | 2.5   |
| K       | 0     |
| Mg      | 1.5   |
| NH$_4$  | 65    |

Into a 25 mL vial, there were added 100 mg of the sample to be tested, to which there were added 10 ml of the above test dialysis solution. The vial was placed in an upright shaker and agitated at 37° C. for about 10–18 hours. The mixture was then filtered and the filtrate analyzed for NH$_4^+$ concentration by ion chromatography. Based on this analysis, the particular sample's ability to ion exchange ammonium ions was determined by calculating the ammonium (NH$_4^+$) distribution coefficient (K$_d$) by using the following formula:

$$K_d(\text{mL}/\text{g}) = \frac{(V)(Ac)}{(W)(Sc)}$$

where: V=volume of test dialysate (mL)
Ac=concentration of cation absorbed on ion-exchanger (g/mL)
W =mass of ion-exchanger evaluated (g)
Sc =concentration of cation in post reaction supernate (g/mL) The results of the testing are presented in Table 2.

TABLE 2

Ammonium K$_d$ for several molecular sieves

| Sample I.D. | K$_d$ |
|-------------|-------|
| A           | 178   |
| B           | 79    |
| C           | 100   |
| D           | 58    |
| E           | 17    |
| F           | 10    |
| Zeolite W   | 90    |

The results in Table 2 show that the compositions of the present invention have a wide range of K$_d$ for ammonium ion and are suitable for removing toxins from blood.

We claim as our invention:

1. A process for removing toxins from a fluid selected from the group consisting of blood and dialysate solution comprising contacting the fluid containing the toxins with a microporous ion exchanger at ion exchange conditions thereby removing the toxins from the fluid, the microporous ion exchanger selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

and $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$.

2. The process of claim 1 where the fluid is blood.

3. The process of claim 1 where the fluid is a dialysate solution.

4. The process of claim 1 where M is tin (+4).

5. The process of claim 1 where M is titanium (4+).

6. The process of claim 1 where M is niobium (5+).

7. The process of claim 1 where n=0.

8. The process of claim 1 where A is a mixture of calcium and sodium.

* * * * *